(12) United States Patent
Lau et al.

(10) Patent No.: US 11,690,711 B2
(45) Date of Patent: Jul. 4, 2023

(54) COLOR-CODED PROSTHETIC VALVE SYSTEM AND METHODS FOR USING THE SAME

(71) Applicant: Edwards Lifesciences Corporation, Irvine, CA (US)

(72) Inventors: Jackie P. Lau, Anaheim, CA (US); John C. Peterson, Ladera Ranch, CA (US); Grace Myong Kim, Garden Grove, CA (US); John F. Migliazza, Belmont Shores, CA (US); Travis Zenyo Oba, Yorba Linda, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 902 days.

(21) Appl. No.: 16/589,014

(22) Filed: Sep. 30, 2019

(65) Prior Publication Data
US 2020/0030087 A1 Jan. 30, 2020

Related U.S. Application Data

(63) Continuation of application No. 13/215,576, filed on Aug. 23, 2011, now Pat. No. 10,426,606.

(60) Provisional application No. 61/376,147, filed on Aug. 23, 2010.

(51) Int. Cl.
*A61F 2/24* (2006.01)
*A61F 2/00* (2006.01)

(52) U.S. Cl.
CPC .......... *A61F 2/2412* (2013.01); *A61F 2/2427* (2013.01); *A61F 2/0095* (2013.01); *A61F 2/2418* (2013.01); *A61F 2/2496* (2013.01); *A61F 2250/0064* (2013.01); *A61F 2250/0087* (2013.01); *A61F 2250/0097* (2013.01)

(58) Field of Classification Search
CPC ............ A61F 2250/0087; A61F 2/2409; A61F 2/2427
USPC ........................................................ 623/2.11
See application file for complete search history.

(56) References Cited

U.S. PATENT DOCUMENTS

| | | | |
|---|---|---|---|
| 4,702,250 A | 10/1987 | Ovil et al. | |
| 4,898,155 A | 2/1990 | Ovil et al. | |
| 5,573,529 A * | 11/1996 | Haak ...................... | A61B 90/92 606/1 |
| 5,824,068 A | 10/1998 | Bugge | |
| 6,223,440 B1 * | 5/2001 | Rashman ............... | A61B 90/94 30/340 |

(Continued)

*Primary Examiner* — Martin T Ton
(74) *Attorney, Agent, or Firm* — Guy Cumberbatch

(57) ABSTRACT

A color-coded bioprosthetic valve system having a valve with an annular sewing ring, and a valve holder system with a holder sutured to the ring of the valve, a post operatively connected to the holder, and an adapter sutured to the post and having a color associated with the valve model and/or size. For example, the adapter may be blue to indicate that the valve of the system is a mitral valve of a particular type and/or size. The system may also include a flex handle that is configured to engage with the adapter. The handle has a color associated with the adapter such that a user is able to visually determine that the handle color matches the valve model. For example, the handle may have a grip that is colored blue to match the blue color of the adapter. Accordingly, the color-coded system enables users to confirm easily that the correct accessories such as the sizer or flex handle are being used with the correct valve.

20 Claims, 7 Drawing Sheets

(56) References Cited

U.S. PATENT DOCUMENTS

| | | | |
|---|---|---|---|
| 6,668,751 B1* | 12/2003 | Henke | B25G 1/00 81/177.1 |
| 6,966,925 B2* | 11/2005 | Stobie | A61F 2/2427 623/2.11 |
| 7,351,197 B2 | 4/2008 | Montpetit et al. | |
| 7,922,711 B2* | 4/2011 | Ranalletta | A61M 39/26 604/539 |
| 2003/0047126 A1* | 3/2003 | Tomaschko | A61B 90/92 116/200 |
| 2004/0122462 A1* | 6/2004 | Bakos | A61M 16/0429 606/191 |
| 2004/0148017 A1 | 7/2004 | Stobie | |
| 2005/0085904 A1* | 4/2005 | Lemmon | A61F 2/2427 623/2.11 |
| 2006/0004398 A1 | 1/2006 | Binder et al. | |
| 2006/0004406 A1* | 1/2006 | Wehrstein | A61B 17/28 606/205 |
| 2006/0155321 A1 | 7/2006 | Bressler et al. | |
| 2006/0241743 A1 | 10/2006 | Bergin et al. | |
| 2006/0271000 A1 | 11/2006 | Ranalletta et al. | |
| 2012/0142798 A1* | 6/2012 | Thompson | C08J 9/30 521/154 |

* cited by examiner

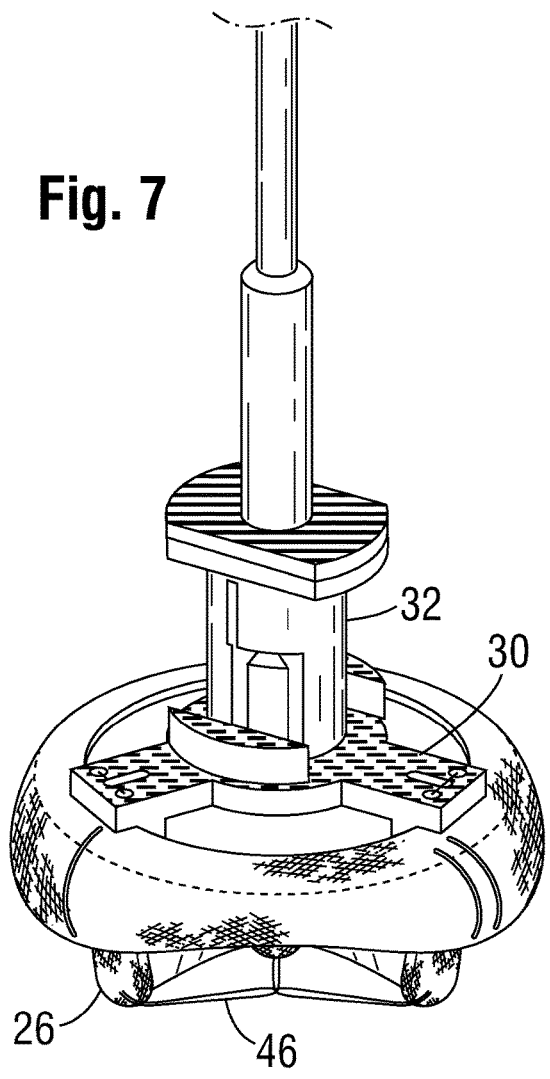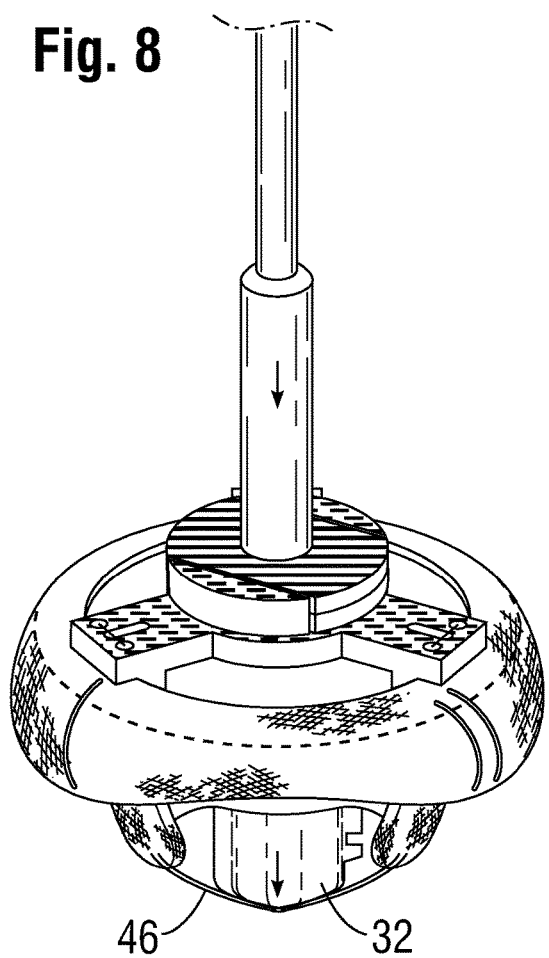

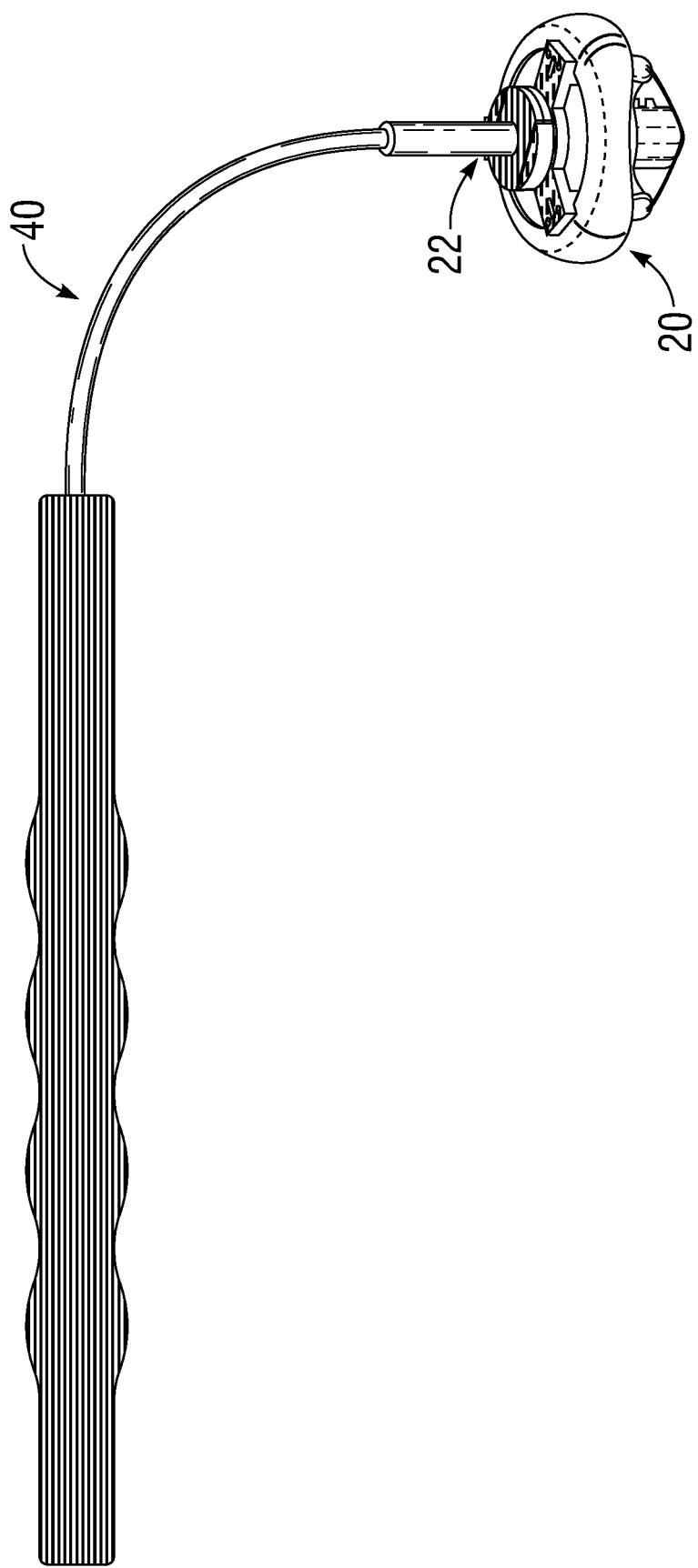

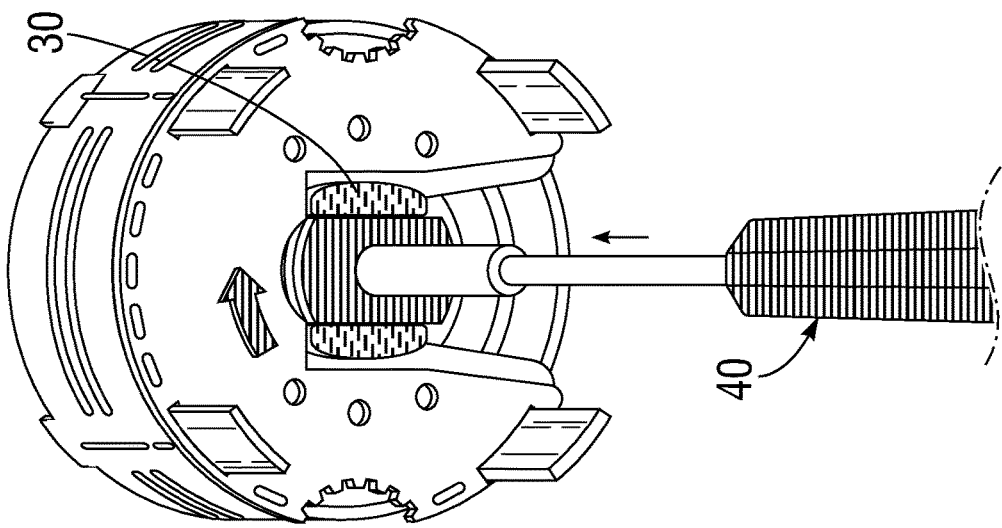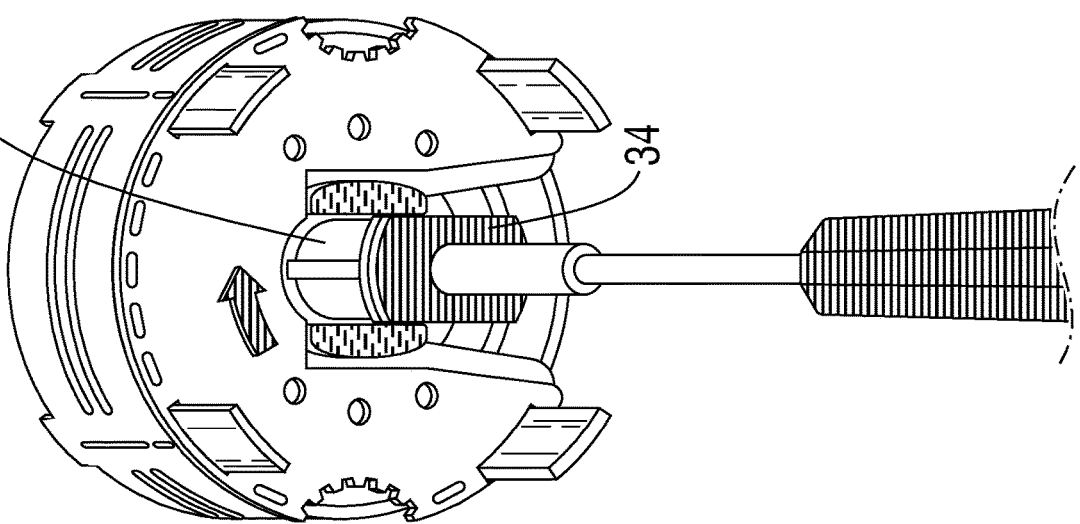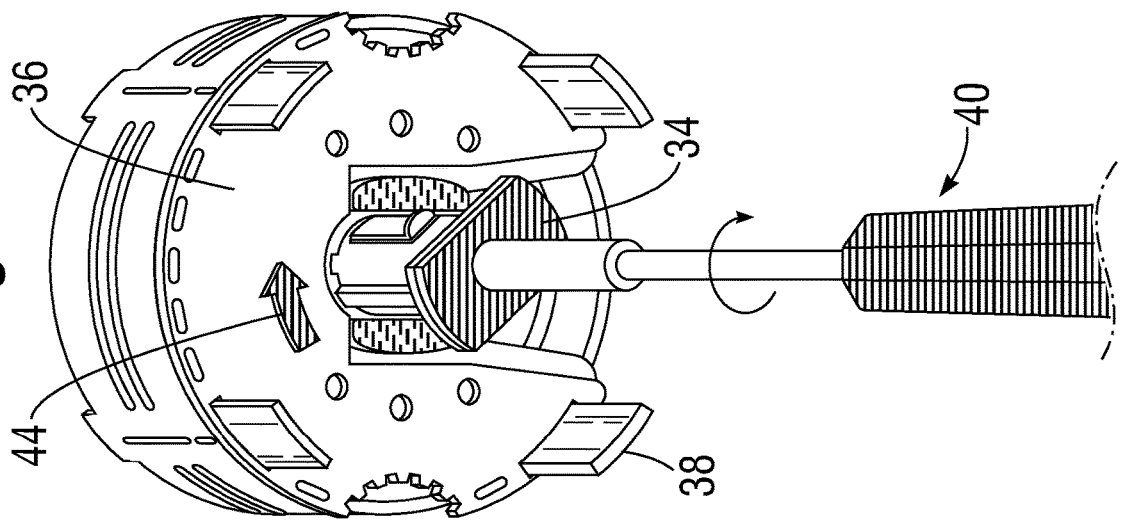

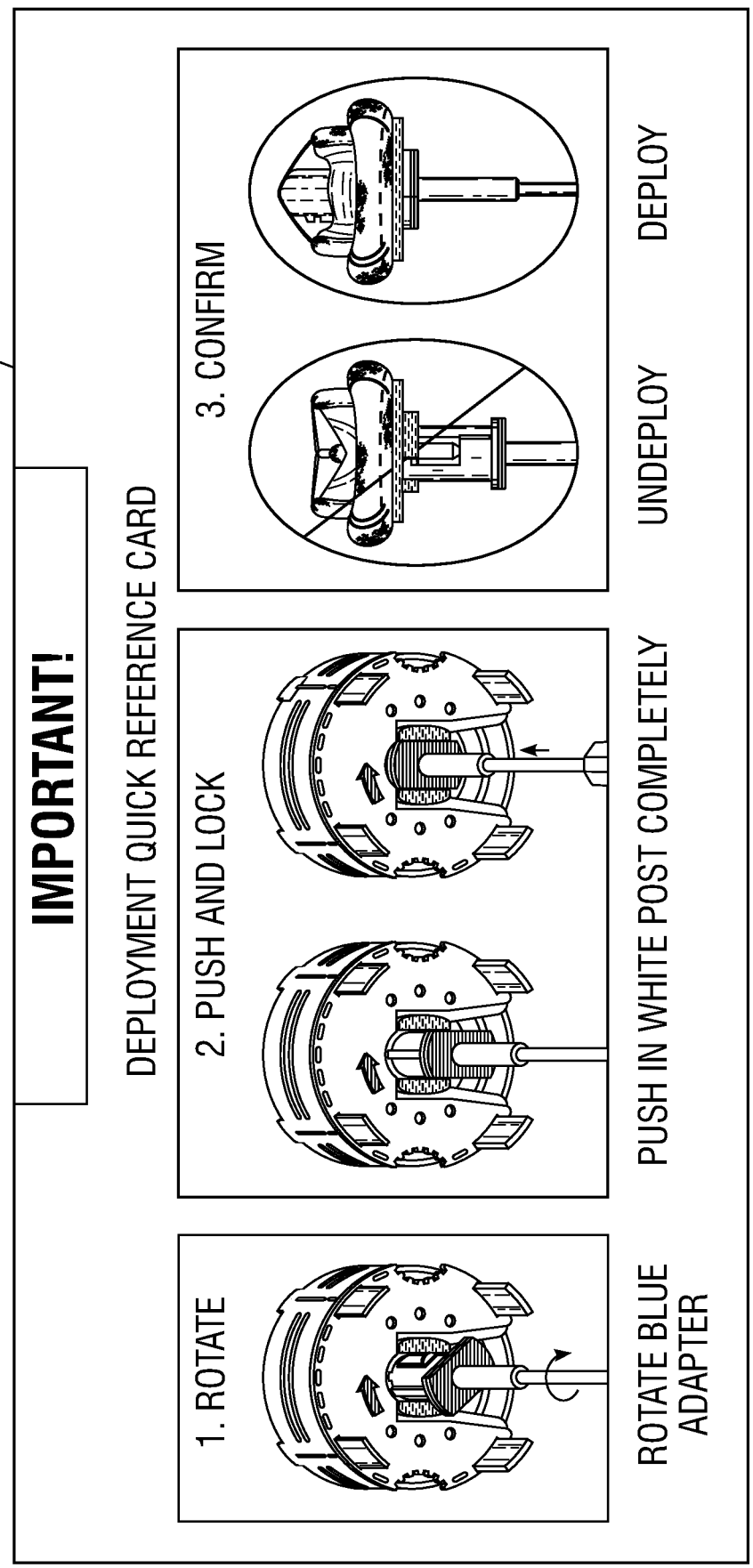

COLOR-CODED PROSTHETIC VALVE SYSTEM AND METHODS FOR USING THE SAME

CROSS REFERENCE TO RELATED APPLICATIONS

This application is a continuation of U.S. application Ser. No. 13/215,576, filed Aug. 23, 2011, now U.S. Pat. No. 10,426,606, which claims the benefit of U.S. Application No. 61/376,147, filed Aug. 23, 2010, the contents all of which are expressly incorporated by reference herein for all purposes.

FIELD OF THE INVENTION

The present invention relates generally to devices and procedures related to heart valve replacement, and, more particularly, to a color-coded prosthetic valve system.

BACKGROUND OF THE INVENTION

The most common flexible leaflet valve construction includes three leaflets mounted to commissure posts around a peripheral non-expandable support structure with free edges that project toward an outflow direction and meet or coapt in the middle of the flowstream. A suture-permeable sewing ring is provided around the inflow end.

The most successful bioprosthetic materials for flexible leaflets are whole porcine valves and separate leaflets made from bovine pericardium stitched together to form a tri-leaflet valve. Bioprosthetic heart valves are packaged in jars filled with preserving solution for shipping and storage prior to use in the operating theater. To minimize the possibility of damage to the relatively delicate bioprosthetic heart valves, they are stabilized with bracketing structure to prevent them from striking the inside of the jar. The valves are stabilized with various structures, including a 2- or 3-piece clip and tubular sleeve structure, such as shown in U.S. Pat. No. 6,416,547 to Erickson, et al.

Bioprosthetic valves typically have a delivery holder centrally located and sutured thereto, and an elongated delivery handle couples to the holder for manipulating the valve assembly during implant. The holder is attached to the inflow sewing ring for mitral valves and to the inflow cusps or outflow commissure tips for aortic valves.

Mitral valve replacement is the most common when moderate to severe calcification is present on the leaflets. When implanting a valve in the mitral position the valve is inverted with the inflow side facing the surgeon. Due to this less visible and somewhat difficult implant configuration, ease of the implant and suturing procedure is more important.

When placing a tissue type prosthetic valve in the mitral position, the commissure posts are on the distal or blind side of the valve and may become entangled with pre-installed anchoring sutures, potentially damaging the annulus or tissue valve during delivery. Some attempts have been made to overcome these problems in current holders for prosthetic mitral valves. An example of such a holder is U.S. Pat. No. 4,865,600, Carpentier, et al., incorporated herein by reference, and another similar device is seen in U.S. Pat. No. 6,966,925 to Stobie which includes a shaft member positioned on the holder that is axially movable just prior to valve deployment to cause lengths of holder-valve attachment sutures to extend axially beyond the commissure posts in the fashion of a tent, thereby preventing looping of an array of pre-implanted anchoring sutures around the commissure posts.

Because of the complexity of certain bioprosthetic valve systems, there is a continued need in the art for enhancements to ease the use of such systems for the operating room staff and surgeon.

SUMMARY OF THE INVENTION

According to one aspect of the invention, a color-coded bioprosthetic valve system may include a bioprosthetic valve and a valve holder system. Color coding facilitates training of O.R. staff in procedural steps and correct identification of components used in a valve/accessory system.

The valve typically has an internal stent and an annular sewing ring on an inflow end, and is of a particular valve model, such as a mitral valve of a labeled size. The valve holder system may include a holder sutured to the ring of the valve, a post operatively connected to the holder, and an adapter sutured to the post and having a color associated with the valve model. For example, the adapter may be blue to indicate that the valve of the system is a mitral valve. The system may also include a flex handle that engages with the adapter. The handle has a color associated with the adapter such that a user is able to visually determine that the handle color matches the valve model. For example, the handle may have a grip that is colored blue to match the blue color of the adapter. Accordingly, the color-coded system enables users to confirm easily that the correct accessories such as the sizer or flex handle are being used with the correct valve.

According to another aspect, the holder, the post, and the adapter may each have a color that is in contrast to each other such that the holder is visually distinguishable from the post and the adapter, and the post is visually distinguishable from the adapter. This color contrast may aid a user to confirm that proper deployment has been obtained. For example, the holder may be grey, the post white, and the adapter blue, and proper deployment may be confirmed by inspecting that the white post or blue adapter abuts or is flush with the gray holder.

The Magna Mitral Ease from Edwards Lifesciences is one particular heart valve that includes various design features for easier implantation. For example, the valve system includes a tri-colored holder and a unique suture guide line, as described herein, and a wide, saddle-shaped cuff. This new mitral bovine pericardial heart valve also features a holder that makes an audible click to indicate the valve has been properly rotated and set into place. However, it is the color visual cues with easy-to-follow instructions on the quick reference card which makes procedure preparation extremely straightforward.

In a preferred embodiment, a color-coded prosthetic heart valve system comprises a heart valve of a labeled size, and a heart valve holder system. The holder system has a stationary part in a first color attachable to the heart valve and having at least two movable parts that are movable with respect to the stationary part in a second color distinct from the first color. One of the two movable parts may comprise a flex handle that engages with the other movable part of the valve holder system, wherein a grip of the flex handle is in the second color. The valve holder system may further include a jar clip in a third color to which the stationary part is operatively removable for protection within a storage jar, the jar clip having a movement indicator thereon in the second color that indicates the direction of movement of the movable part relative to the stationary part. The heart valve system desirably also has an annulus sizer having a grip in the second color, the second color being associated with the labeled valve size.

The heart valve may include a stent on an inflow end, flexible commissures projecting from the stent in an outflow direction, and flexible leaflets distributed about a valve axis and supported between the flexible commissures. The stationary part preferably comprises a holder attached to an inflow side of the valve, and one of the two movable parts comprises a proximal end of a post that translates along the valve axis with respect to the holder and passes through a central bore in the holder. The heart valve holder system further including filaments that are attached to the holder and extend through the heart valve and cross over between tips of the flexible commissures, wherein a distal end of the post contacts the filaments along the valve axis so as to push them in a distal direction and flex the commissure tips inward. The holder is desirably sutured to a sewing ring on an inflow side of the valve, and the proximal end of the post comprises an adapter sutured to the post, the adapter having the second color. Preferably, the holder, the post, and the adapter each have a color that is in contrast to one another such that the holder is visually distinguishable from the post and the adapter, and the post is visually distinguishable from the adapter.

Another color-coded prosthetic heart valve system comprises a heart valve of a labeled size, and a heart valve holder system attachable to the heart valve. The holder system includes a first stationary part in a first color and a first movable part that is movable with respect to the stationary part in a second color distinct from the first color, and a second stationary part including a movement indicator thereon in the second color that indicates the direction of movement of the first movable part relative to the second stationary part. A second movable part in the second color preferably comprises a flex handle that engages with the first movable part of the valve holder system, wherein a grip of the flex handle is in the second color. The second stationary part may be a jar clip in a third color to which the first stationary part is operatively removable for protection within a storage jar. In a preferred embodiment, the heart valve system further includes an annulus sizer having a grip in the second color, the second color being associated with the labeled valve size.

The heart valve may include a stent on an inflow end, flexible commissures projecting from the stent in an outflow direction, and flexible leaflets distributed about a valve axis and supported between the flexible commissures. The first stationary part desirably comprises a holder attached to an inflow side of the valve, wherein the heart valve holder system further including filaments that are attached to the holder and extend through the heart valve and cross over between tips of the flexible commissures. Further, the first movable part preferably comprises a proximal end of a post that first rotates about and then translates along the valve axis with respect to the holder and passes through a central bore in the holder. A distal end of the post contacts the filaments along the valve axis so as to push them in a distal direction and flex the commissure tips inward, the movement indicator showing the direction to rotate the post to enable it to translate along the valve axis. The holder may be sutured to a sewing ring on an inflow side of the valve, and the proximal end of the post may comprise an adapter sutured to the post, the adapter having the second color. Preferably, the holder, the post, and the adapter each have a color that is in contrast to one another such that the holder is visually distinguishable from the post and the adapter, and the post is visually distinguishable from the adapter.

A method of deploying a heart valve system is also provided including first obtaining a color-coded prosthetic heart valve system, the system comprising:

a heart valve of a labeled size including a stent on an inflow end, flexible commissures projecting from the stent in an outflow direction, and flexible leaflets distributed about a valve axis and supported between the flexible commissures; and a heart valve holder system attachable to the heart valve having a holder attached to an inflow side of the valve in a first color, a first movable part that is movable with respect to the holder in a second color distinct from the first color, and a second stationary part including a movement indicator thereon in the second color that indicates the direction of movement of the first movable part relative to the second stationary part, The method includes displacing the first movable part as indicated by the movement indicator and causing the first movable part to flex tips of the valve commissures inward. The heart valve holder system desirably includes filaments that are attached to the holder and extend through the heart valve and cross over between tips of the flexible commissures. The first movable part may be a proximal end of a post that first rotates about and then translates along the valve axis with respect to the holder and passes through a central bore in the holder, wherein a distal end of the post contacts the filaments along the valve axis so as to push them in a distal direction and flex the commissure tips inward, the movement indicator showing the direction to rotate the post to enable it to translate along the valve axis. Desirably, a second movable part in the second color comprises a flex handle that engages with the first movable part of the valve holder system, wherein a grip of the flex handle is in the second color, and the method further comprises screwing the handle into the first movable part and using the handle to displace the first movable part. The first movable part may comprise a proximal end of a post that first rotates about and then translates along the valve axis with respect to the holder and passes through a central bore in the holder. The method therefore includes fully screwing the flex handle into the proximal end of the post and then further rotating the flex handle as indicated by the movement indicator, thereby also rotating the post until the post can be translated axially. In one embodiment, the proximal end of the post comprises an adapter sutured to the post, the adapter having the second color, the method including severing sutures connecting the adapter to the post and detaching the adapter and flex handle from the post. Furthermore, the flex holder, the post, and the adapter each may have a color that is in contrast to one another such that the holder is visually distinguishable from the post and the adapter, and the post is visually distinguishable from the adapter.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIG. 7 illustrates a color-coded assembly shown in an undeployed position according to a number of embodiments and including a distal portion of a flex handle connected to a bioprosthetic valve, particularly including, for example, an adapter with blue coding, a post with white coding, and a holder with gray coding;

FIG. 8 illustrates the assembly of FIG. 7 in a deployed position, enabling user confirmation of proper deployment, for example, by inspection that the blue-coded adapter is flush with the gray-colored holder;

FIG. 9 is a perspective view of the deployed assembly of FIG. 8, particularly illustrating the flex handle having molded grip with blue coding that matches the blue coding of the adapter, thereby enabling easy user confirmation that this particular flex handle is being properly used with this particular valve model;

FIGS. 10A, 10B, and 10C illustrate a color-coded assembly according to still other embodiments, respectively showing sequential stages of a valve subassembly with holder system being unlocked and deployed, particularly illustrating a blue-coded arrow indicia on the clip indicating to a user a direction that a blue-coded flex handle should be rotated so that a blue-coded adapter rotates in the proper direction for unlocking; and FIG. 11 illustrates a reference card according to a number of embodiments, showing, for example, the steps for proper deployment of a valve subassembly.

DETAILED DESCRIPTION OF THE PREFERRED EMBODIMENTS

Figure 1:
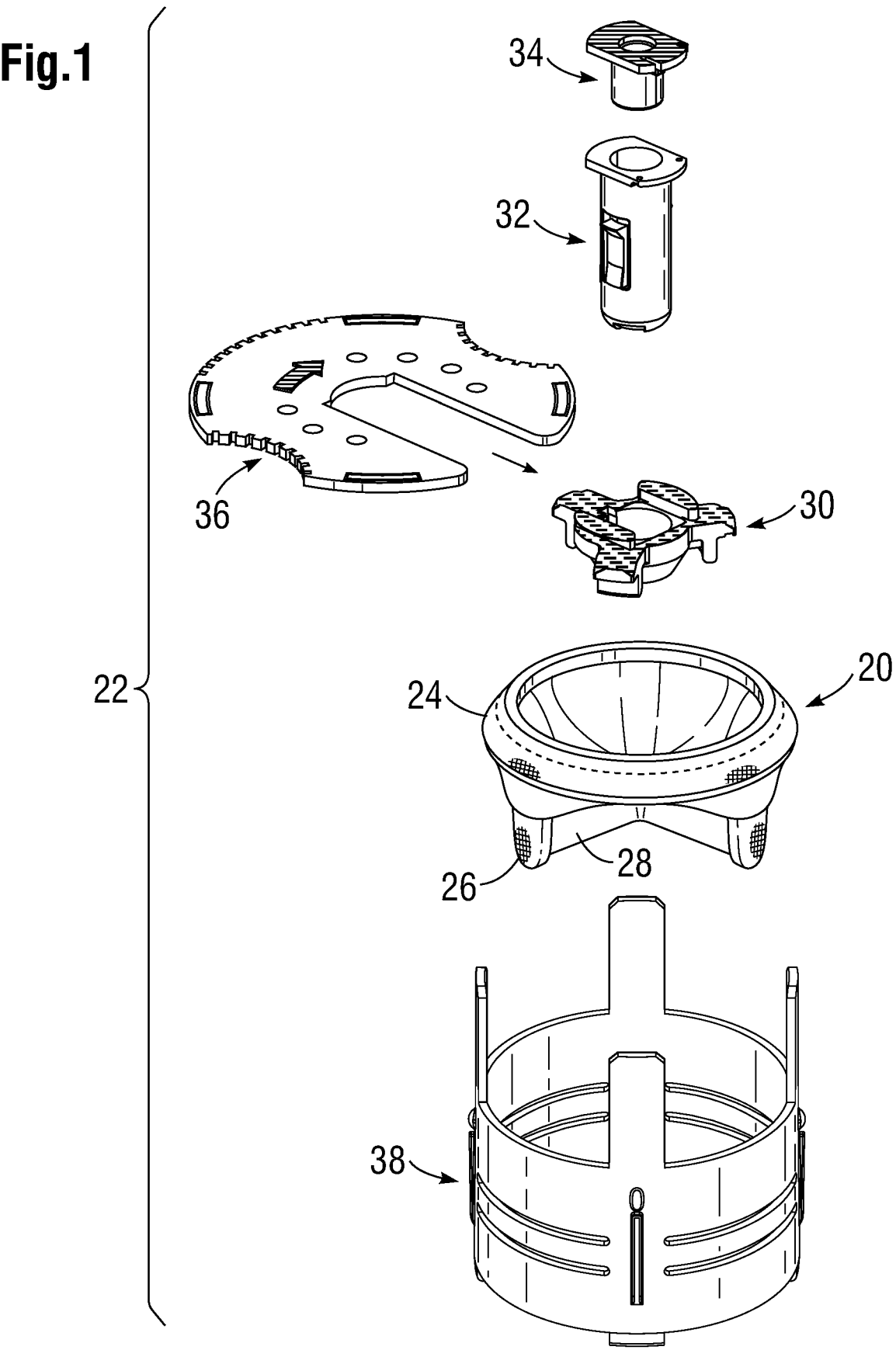
FIG. 1 illustrates a system for heart valve replacement according to a number of embodiments.
Figure 2:
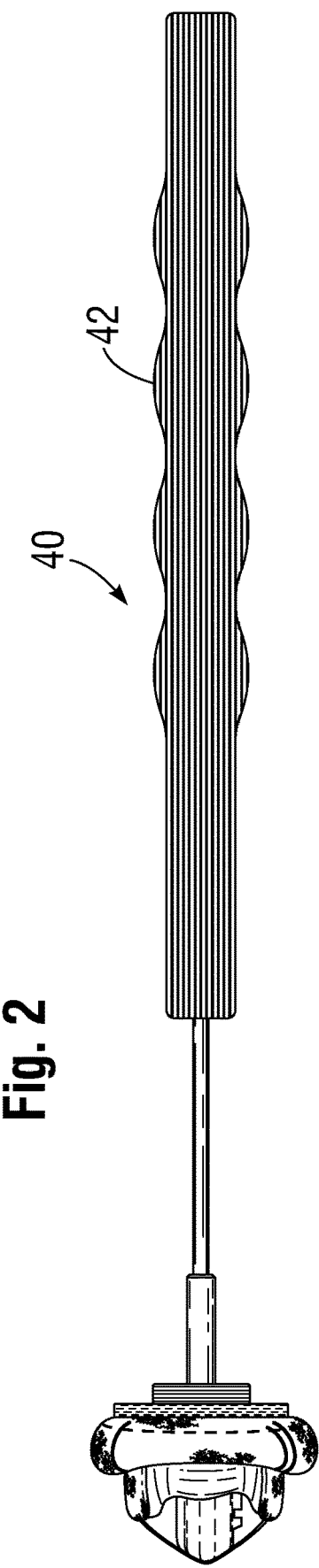
FIG. 2 illustrates a color-coded flex handle according to still other embodiments, including, for example, a blue grip.
Figure 3:
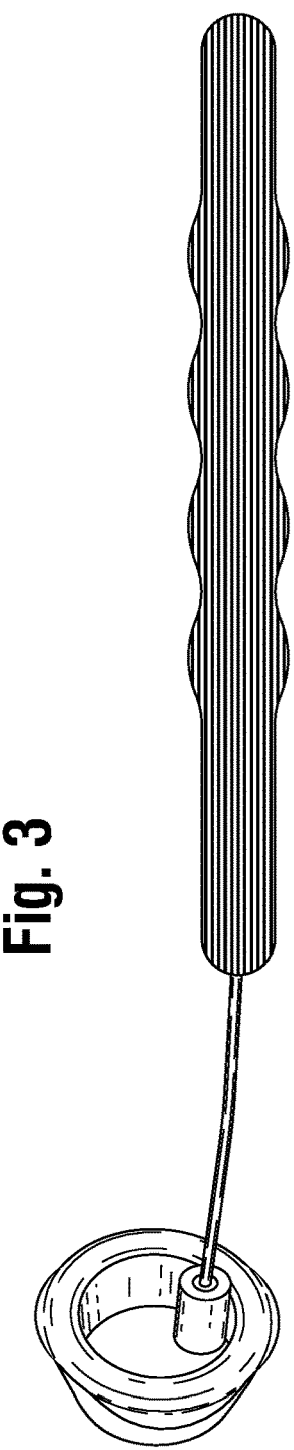
FIG. 3 illustrates a color-coded valve annulus sizer according to other embodiments, including, for example, a blue grip.

Referring to the drawings in detail, a color-coded bioprosthetic mitral valve and holder system is shown in FIGS. 1-3 according to a number of embodiments. The system may include a prosthetic valve 20 and a valve holder system 22. The valve 20 has a labeled size (typically between 25 and 33 mm in 2 mm increments) and is of a particular valve model, such as a mitral valve of a particular type (e.g., the Magna Mitral Ease system available from Edwards Lifesciences of Irvine, Calif.). The valve 20 has an annular sewing ring 24 on an inflow end, an internal stent (not shown) with generally axially-directed commissures 26 projecting in an outflow direction, and a plurality of flexible leaflets 28 distributed about a central valve axis and supported by the commissures, thus providing occluding surfaces within the valve orifice.

The valve holder system 22 may include a holder 30 sutured to the sewing ring 24 of the valve, a post 32 operatively connected to the holder, and an adapter 34 sutured to the post and having a color associated with the valve model and/or size. For example, in some of the embodiments, the adapter may be blue to indicate that the valve of the system is a Magna Mitral Ease valve. Additionally, shades of one color, different colors, or colors with distinctive cross-hatching, for instance, may be used to distinguish valves of different sizes within a line of valves. The holder attaches to a clip 36 which couples to a ribbed sleeve 38 to protect the valve from damage inside a storage jar (see 35 in FIG. 4). Greater details of such a holder and storage system can be found in U.S. Pat. No. 6,966,925 to Stobie, which disclosure is expressly incorporated herein.

The system may also include a flex handle 40 as shown in FIG. 2 that engages with the adapter 34 on the proximal end of post 32. According to a number of embodiments, the handle 40 has a color associated with the adapter 34 such that a user is able to visually determine that the handle color matches the valve model and/or size. For example, as shown particularly in FIG. 2, the handle 40 may have a grip 42 that is a color such as blue to match the blue color of the adapter 34. Accordingly, the color-coded system enables users to confirm easily that the correct accessories (such as a sizer in FIG. 3) or the correct valve is being used with the handle, which is also shown in FIG. 9. (It should be noted that since color cannot usually be shown in patent drawings, different colors are indicated with particular shading as set forth in the Patent Office drawing guidelines, MPEP § 608.02).

Figure 4:
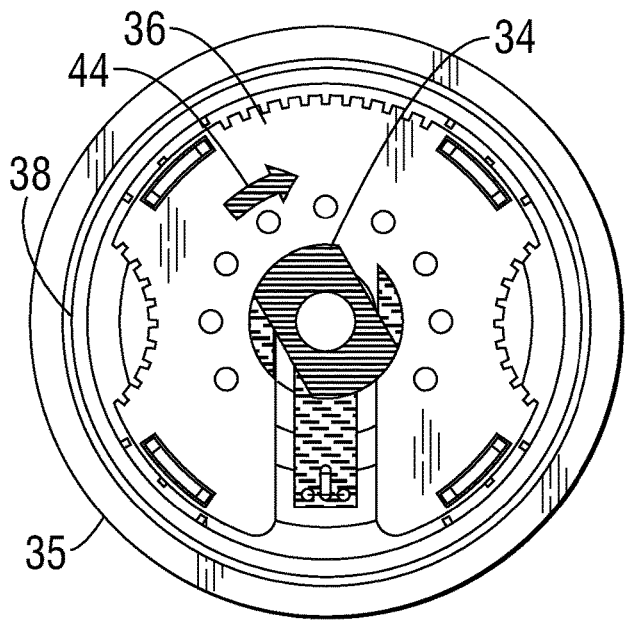
FIG. 4 illustrates a bioprosthetic valve with a color-coded clip and arrow indicia according to some of the embodiments.

In additional embodiments such as shown in FIGS. 1 and 4, the valve holder system 22 may also include a clip 36 from which the holder 30 is operatively removable. The clip 36 may have colored movement indicia 44 such as an arrow indicating to a user a direction to rotate the handle 40 to engage with the adapter 34, and for actuating a valve commissure constriction mechanism as will be explained.

The components shown in FIG. 1 are assembled together in a valve jar. When the nurse or technician opens the jar, they must perform the following steps, as seen in FIGS. 10A-10C, to deploy the holder system prior to handing the valve off to the surgeon for implantation:

Screw handle into the Adapter until handle is fully engaged.

Continue to rotate handle clockwise until the Adapter & Post unlocks in the Holder.

Pull the assembly (Valve, Clip, Holder, Post, and Adapter) from the jar.

Push the Post through the Holder to deploy the holder system.

While the surgeon is implanting the valve, several steps he/she performs are:

To remove the Adapter/Handle: cut the attached suture thread and pull off the Adapter/Handle.

To remove the Holder/Post from the Valve: cut the three attached suture threads and pull off the Holder/Post.

In the illustrated embodiment, the adapter 34 attaches with sutures to the proximal end of the post 32, and can be severed and removed therefrom while the post remains locked in the position constricting the valve commissures. This enables the handle 40 to be easily removed without having to unscrew it. However, the adapter 34 may be eliminated such that the distal end of the handle 40 engages the proximal end of the post 32 directly, which would then be also colored blue. In terms of the user, the colored-coded "proximal end of the post" is therefore either the post 32 or the adapter 34 thereon.

To deploy the holder system such that the valve commissures 26 constrict, the post 32 translates through the valve orifice, as seen in FIGS. 7 and 8. More particularly, the holder 30 attaches to the inflow side of the valve 20 and is thus stationary. The holder as seen in FIG. 1 has a central bore. The post 32 translates along the valve axis with respect to the holder 30 and passes through the central bore therein. The heart valve holder system further including filaments 46 that are attached to the holder 30, extending through the heart valve 20 and crossing over along the central valve axis between tips of the flexible commissures 26. The distal end of the post 32 eventually contacts the filaments 46 along the valve axis so as to push them in a distal direction and flex the commissure tips inward. It should be understood that this is just one embodiment of commissure constriction, and other mechanisms with relatively moving parts may benefit from being color-coded. Furthermore, other mechanisms for manipulating the valve or holder, or that simply facilitate manual handling of the holder system and valve may benefit from a color-coding system as described herein.

In still other embodiments such as shown in FIGS. 1, 5, 7 and 8, the holder 30, the post 32, and the adapter 34 may each have a color that is in contrast to each other such that the holder is visually distinguishable from the post and the adapter, and the post is visually distinguishable from the adapter. For instance, the stationary holder 30 may be a first color (e.g., grey) and the adapter 34 (or proximal end of the post 32) is a second, distinct color (e.g., blue). Further, the post 32 may be a third color (e.g., white) distinct from the first and second colors. Also, it should be noted that the post 32 and adapter 34 are movable with respect to the holder 30, which in turn is fixed to the valve 20, so there are distinct colors for relatively movable parts.

As particularly shown in FIG. 8, this color contrast may aid a user to confirm that proper deployment has been obtained, by inspecting that the white post 32 or blue adapter 34 abuts or is flush with the gray holder 30. A further aid may be provided in the form of instructions that refer not just to the relatively movable parts but also to their respective colors (see below). Since the user views the assembly from the top, as in FIG. 4, it is difficult to see the white post 32 from this perspective because of the blue adapter 34 on its proximal end. So the user should look for the blue adapter 34 to be flush with the top of the gray holder 30 (there are two wings slightly raised on the top of the holder, and the top of the blue adapter is generally at the same level as the top of the two wings of the holder).

Figure 6A:
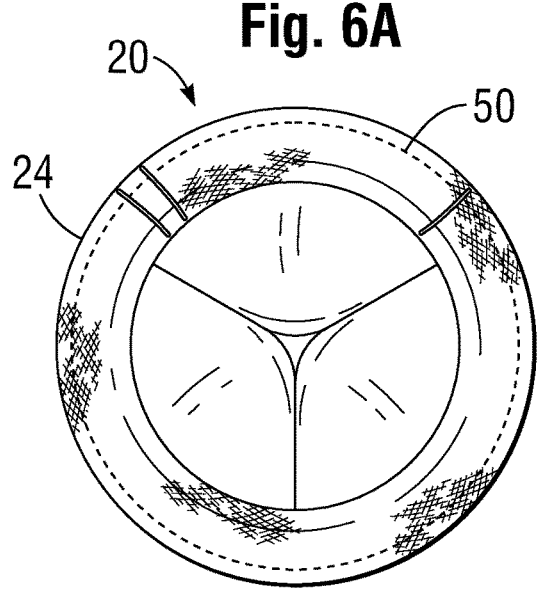
FIGS. 6A and 6B illustrate respective embodiments of a bioprosthetic valve with suture guidelines.
Figure 6B:
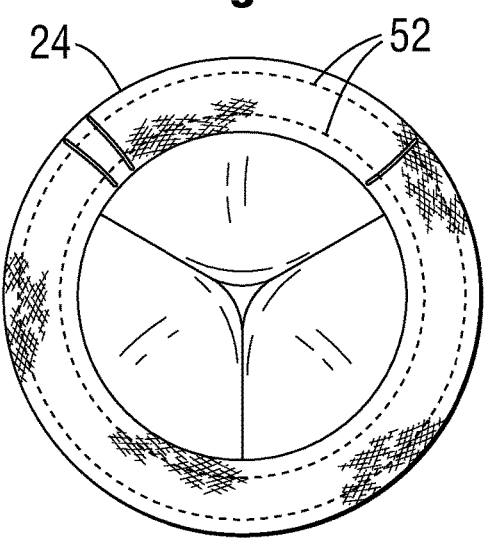

In further embodiments as shown in FIGS. 6A and 6B, the valve 20 may include an annular sewing ring 24 with indicia for indicating suture placement. For example, as shown in FIG. 6A, the indicia may include a single guideline 50 disposed on the annular ring to indicate the desired suture location. Alternatively, as shown in FIG. 6B, the indicia may include a pair of concentric guidelines 52 disposed on the annular ring 24 to indicate boundaries of an acceptable suture zone.

To use the valve system, the flex handle 40 may be screwed into the adapter 34 as shown in FIG. 10A. The blue arrow movement indicator 44 of the clip 36 indicate to the user to rotate the handle 40 clockwise as shown for engagement, which is also shown in FIG. 4. The handle 40 may be continued to be rotated as indicated by the blue arrow indicia of the clip 36, thereby also rotating the adapter 34 and the post 32 until the post unlocks in the holder as shown in FIG. 10B. That is, the post 32 is prevented from translating axially until it has been rotated a certain angular extent. The handle 40 may then be urged toward the holder 30 as shown by the arrow in FIG. 10C, thereby urging the post 32 through the holder 30 until it is fully seated in the holder, thereby deploying the valve holder system as shown in FIG. 8.

According to additional embodiments, the system may also include a deployment quick reference card 60 as shown in FIG. 11 to aid the user in performing these operations. The reference card may provide instructions by indicating to colors of, for example, the adapter, the post, the holder, rather than specific names of such elements, to further facilitate the easy use of the system.

Figure 5:
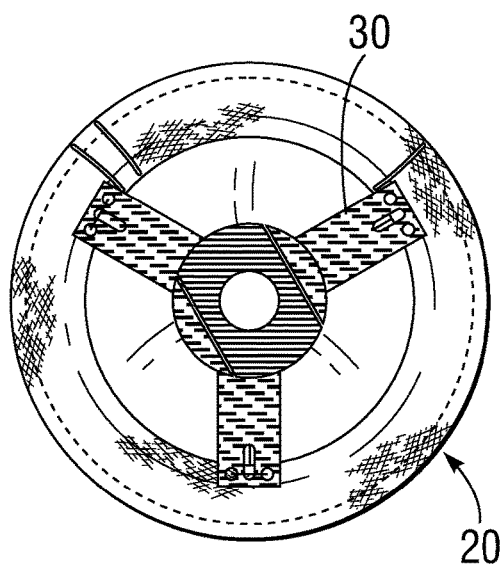
FIG. 5 illustrates a bioprosthetic valve with a color-coded system including a blue adapter and grey holder.

To further utilize the system, the suture thread connecting the adapter to the holder as shown in FIGS. 4 and 5 may be cut to remove the handle and the adapter from the holder. In addition, the suture thread connecting the holder to the annular ring of the valve, as particularly shown in FIG. 5, may be cut to remove the holder and the post from the valve.

In view of the foregoing description, the color-coded system eases training and provides intuitive deployment for the operating room staff and surgeon. The multi-color delivery system may incorporate color schemes among the features of the valve, the holder, accessories, and packaging to clearly indicate complementary parts. At the same time, contrasting color schemes increase visibility of separate components. In addition, color coding facilitates operating training as the instruction card may refer to parts and features in terms of color, rather than using terms unfamiliar to the user or longer descriptions of component features or geometry.

Color coding the different components may improve training in the following areas:

1. O.R. Staff:

Matching components/accessories with the correct valve/accessory system. For example, the Magna Mitral Ease system available from Edwards Lifesciences of Irvine, Calif. is characterized by the blue color of the accessory handles, the blue Adapter, and the blue arrow on the Clip. Other valve/accessories may use another color for differentiation.

Ease in learning and remembering the different components in the holder system for deployment. For example, components are referred to in terms of part name AND color rather than just potentially unfamiliar phrases such as "Holder", "Post", "Adapter", etc. This improves clarity when training users as familiar colors would be easy to refer to when training and easy to remember when referring to a reference card as shown in FIG. 11.

Ease in learning, remembering, and confirming holder system steps. For example, color coding can clarify directional information for actions required. The blue arrow on the Clip pointed in the clockwise direction highlights the fact that the user must turn the blue Handle and the blue Adapter in the clockwise direction. Another example is that the user must perform a visual inspection to confirm an action—be sure that the blue part (Adapter) is flush with the gray part (Holder). Additionally color contrast between components may provide additional visual cues into how each part interacts with other parts, defining extent and fit of each part into one another and making apparent each component's function.

2. Surgeons:

Ease in identifying the correct suture threads to cut to release the Adapter/Handle, or the Holder/Post. For example, the surgeon could be told to cut the suture on the blue part first (i.e. Adapter) to remove the Handle (and not to cut the suture on the gray part, i.e. Holder).

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A color-coded prosthetic heart valve delivery system, comprising:

an implantable prosthetic heart valve of a particular model among different models associated with a manufacturer;

a valve holder having a stationary part in a first color attached to the heart valve with sutures to form an assembly, wherein the valve holder further has a movable part with a proximal end in a second color distinct from the first color and visible from a proximal end of the assembly, the movable part being movable with respect to the stationary part from an undeployed position to a deployed position, wherein the movable part is configured to convert the heart valve to a delivery configuration when moved to the deployed position; and a valve delivery handle having a distal end adapted to engage the proximal end of the movable part and convert the heart valve to its delivery configuration, the handle having a grip in the second color.

2. The delivery system of claim 1, wherein the second color is associated with the particular model of heart valves and is distinct from colors used on valve holders and handles for other models of heart valves of the manufacturer.

3. The delivery system of claim 1, wherein the delivery system further includes a storage jar sleeve configured to protect the heart valve from damage inside a storage jar, the sleeve having a jar clip on one end in a color distinct from the second color, wherein the jar clip and valve holder are visible from above when they are within the storage jar, the jar clip having a movement indicator thereon in the second color that indicates an initial direction of movement of the movable part from the undeployed position to the deployed position.

4. The delivery system of claim 3, wherein the movement indicator also indicates the direction of movement of the valve delivery handle to engage the proximal end of the movable part.

5. The delivery system of claim 1, further including a native heart valve annulus sizer having a grip in the second color.

6. The delivery system of claim 1, wherein the heart valve includes flexible stent commissures projecting in an outflow direction, and flexible leaflets distributed about a central valve axis and supported between the flexible commissures, and the stationary part attaches to an inflow side of the valve, wherein the movable part comprises a post that initially rotates about and then translates along the valve axis and passes distally through a central bore of the stationary part to constrict the commissure tips radially inward in the deployed position.

7. The delivery system of claim 6, wherein the heart valve further includes filaments that are attached to the holder and extend through the heart valve and cross over between tips of the flexible commissures, and wherein a distal end of the post contacts the filaments along the valve axis so as to push them in a distal direction and constrict the commissure tips radially inward.

8. The delivery system of claim 6, wherein the proximal end of the post comprises an adapter sutured to the post such that the adapter and valve delivery handle can be removed while the stationary part remains sutured to the heart valve and the post remains locked in the deployed position, the adapter having the second color.

9. The delivery system of claim 8, wherein the holder, the post, and the adapter each has a color that is in contrast to one another such that the holder is visually distinguishable from the post and the adapter, and the post is visually distinguishable from the adapter.

10. The delivery system of claim 1, further including instructions for the converting the heart valve to the delivery configuration that references both each part being manipulated and its color.

11. A color-coded prosthetic heart valve delivery system, comprising:

an implantable prosthetic heart valve of a particular model among different models associated with one manufacturer;

a valve holder having a stationary part in a first color attached to the heart valve with sutures, wherein the valve holder further has a movable part with respect to the stationary part with a proximal end in a second color distinct from the first color, the movable part having a locked position and an unlocked position;

a valve delivery handle having a distal end adapted to engage the proximal end of the movable part; and a storage jar sleeve configured to protect the heart valve from damage inside a storage jar, the sleeve having a jar clip on one end in a color distinct from the second color, wherein the jar clip and valve holder are visible from above when they are within the storage jar, the jar clip having a movement indicator thereon in the second color that indicates the direction of movement of the valve delivery handle to engage the proximal end of the movable part and also an initial direction of movement of the movable part of the valve holder relative to the stationary part from the locked position to the unlocked position.

12. The delivery system of claim 11, wherein the second color is associated with the particular model of heart valves and is distinct from colors used on valve holders and handles for other models of heart valves of the manufacturer.

13. The delivery system of claim 11, wherein the heart valve includes flexible stent commissures projecting in an outflow direction, and flexible leaflets distributed about a central valve axis and supported between the flexible commissures, and the stationary part attaches to an inflow side of the valve, wherein the movable part comprises a post that initially rotates about and then translates along the valve axis and passes distally through a central bore of the stationary part to constrict the commissure tips radially inward in the deployed position.

14. The delivery system of claim 13, wherein the heart valve further includes filaments that are attached to the holder and extend through the heart valve and cross over between tips of the flexible commissures, and wherein a distal end of the post contacts the filaments along the valve axis so as to push them in a distal direction and constrict the commissure tips radially inward.

15. The delivery system of claim 13, wherein the valve holder is configured such that the post is prevented from translating axially until it has been rotated a certain angular extent.

16. The delivery system of claim 13, wherein the proximal end of the post comprises an adapter sutured to the post such that the adapter and valve delivery handle can be removed while the stationary part remains sutured to the heart valve and the post remains locked in the deployed position, the adapter having the second color.

17. The delivery system of claim 16, wherein the holder, the post, and the adapter each has a color that is in contrast to one another such that the holder is visually distinguishable from the post and the adapter, and the post is visually distinguishable from the adapter.

18. The delivery system of claim 11, wherein a grip of the valve delivery handle is in the second color.

19. The delivery system of claim 11, further including a native heart valve annulus sizer having a grip in the second color.

20. The delivery system of claim 11, further including instructions for the converting the heart valve to the delivery configuration that references both each part being manipulated and its color.

* * * * *